(12) United States Patent
Takahashi (10) Patent No.: US 8,374,417 B2
(45) Date of Patent: Feb. 12, 2013

(54) IMAGE PROCESSING METHOD AND RADIOGRAPHIC APPARATUS USING THE SAME

(75) Inventor: Wataru Takahashi, Uji (JP)

(73) Assignee: Shimadzu Corporation, Kyoto (JP)

( * ) Notice: Subject to any disclaimer, the term of this patent is extended or adjusted under 35 U.S.C. 154(b) by 98 days.

(21) Appl. No.: 13/099,414

(22) Filed: May 3, 2011

(65) Prior Publication Data

US 2011/0280463 A1 Nov. 17, 2011

(30) Foreign Application Priority Data

May 14, 2010 (JP) .................. 2010-112313

(51) Int. Cl.
*G06K 9/00* (2006.01)
(52) U.S. Cl. ...................................... 382/132
(58) Field of Classification Search .......... 382/132, 382/260
See application file for complete search history.

(56) References Cited

U.S. PATENT DOCUMENTS

| | | | |
|---|---|---|---|
| 6,072,913 A | 6/2000 | Yamada | |
| 2002/0159623 A1 | 10/2002 | Shinbata | |
| 2006/0171601 A1 | 8/2006 | Shinbata | |

FOREIGN PATENT DOCUMENTS

| | | |
|---|---|---|
| EP | 0 610 604 A1 | 8/1994 |
| JP | 6-301766 A | 10/1994 |
| JP | 7-38758 A | 2/1995 |
| JP | 10-75364 A | 3/1998 |
| JP | 10-171983 A | 6/1998 |
| WO | WO 02/45019 A1 | 6/2002 |
| WO | WO 02/45020 A1 | 6/2002 |

*Primary Examiner* — Duy M Dang
(74) *Attorney, Agent, or Firm* — Cheng Law Group, PLLC (57) ABSTRACT

An image processing method is provided including a band image generation step for generating band images through extracting a portion of frequency components in a source image having a subject image falling thereon; a lowest-frequency image generation step for generating a lowest-frequency image having a lowest-frequency component extracted from the source image; a lowest-frequency image control step for performing conversion processing to the lowest-frequency image in accordance with a lowest-frequency function to generate a lowest-frequency controlled image; a controlled band image generation step for performing conversion processing to the band image in accordance with a high-frequency function, that is different from the lowest-frequency function, to generate a controlled band image; and an image processing step for performing dynamic range compression processing to the source image using the lowest-frequency controlled image and the controlled band image.

22 Claims, 7 Drawing Sheets

IMAGE PROCESSING METHOD AND RADIOGRAPHIC APPARATUS USING THE SAME

BACKGROUND OF THE INVENTION (1) Field of the Invention

This invention relates to a method of processing a radiographic image with a subject image falling thereon, and radiographic apparatus using thereof. More particularly, this invention relates to an image-processing method that allows dynamic range compression processing, and radiographic apparatus using the method.

(2) Description of the Related Art

Medical institutions are equipped with radiographic apparatus for acquiring a subject image with radiation. When an image is subjected to given image processing, the image has an emphasized structure of such as a blood vessel that falls thereon, which may result in easier diagnosis. Accordingly, the conventional radiographic apparatus may process an acquired image through image processing. Specifically, examples of the image processing that radiation photography apparatus may adopt include dynamic range compression processing that controls distribution of pixel values forming an image. See WO2002/045019, WO2002/045202, Japanese Patent Publications No. H10-75364, H10-171983, H7-38758, and H6-301766.

Description will be given of two methods of performing conventional dynamic range compression processing. Upon performing the dynamic range compression processing to a source image having a subject image falling thereon through a first method, firstly a smooth image is generated having high-frequency components in the source image subtracted from the source image. Then, a reverse image is generated having reversed pixel values that form the smooth image while given weighting is performed in accordance with the pixel values. Where this image is added to the source image, the pixel values that form the source image and express wide distribution from a low pixel value to a high pixel value are offset with the reverse image. Consequently, a dynamic range compression processed image (appropriately, simply referred to as a processed image) is generated having a narrowed distribution range of the pixel values.

However, mere superimposing of both the images causes an irregular processed image. The high-frequency components in the source image are removed upon generation of the reverse image. Consequently, the high-frequency components in the source image are not offset, and relatively excessive and highlighted. This may appear in the processed image as an overshot false image.

According to the conventional method, some thought is added upon generating the reverse image. Specifically, absolute values of high-frequency components in the source image are suppressed prior to subtraction of the high-frequency components from the source image. The reverse image generated in this way has a clear boundary line between dark and bright portions. The reverse image is called a high-frequency component stored-smooth image having a part of the high frequency-components in the source image stored therein. This image is added to the source image, whereby no overshoot appears in the processed image.

Let the foregoing method be a first method. The method is expressed as the following equation:

$$P1 = P0 + D_{inv}(P0 - \Sigma LUT) \quad (1)$$

Here, P0 indicates a source image, P1 a processed image, $\Sigma LUT$ high-frequency components in the source image, and $D_{inv}$ a function for generating a reverse image. Moreover, $D_{inv}(P0-\Sigma LUT)$ indicates a high-frequency stored-smooth image.

Moreover, dynamic range compression process includes, as a second method, a method of simply converting pixel values of the source image to generate a conversion image. According to this method, however, not only low-frequency components but also high-frequency components in the source image are removed. Particularly in a portion of the source image with a certain pixel value mentioned later, more high-frequency components are removed to cause a smoothed image in this portion of the processed image. Consequently, the conversion image has deteriorated contrast.

The extent of removing the high-frequency components upon conversion of the source image is determined in accordance with a translation table used when a pixel value of the source image is converted into a pixel value of the processed image. This translation table is table data having a relationship between an input value expressing the pixel value of the source image and an output value expressing the pixel value of the processed image. When seen the input values in the translation table in order from the lower one to the higher one, it is found that the translation table has a portion where the output value hardly varies upon variation of the input values (a low variation portion) and a portion where the output value largely varies upon variation of the input values (a high variation portion.) Moreover, the high-frequency components are remarkably removed upon conversion of the value in the low variation portion in the translation table. The high-frequency components are hardly removed upon conversion of the value in the high variation portion in the translation table.

In view of the state as above, the conventional method adopts a configuration of adding the high-frequency components in the source image to the conversion image. As mentioned above, the high-frequency components in the source image are readily removed from the processed image as the differentiation values are lower in the translation table. Accordingly, such weighting is performed that more high-frequency components in the source image are added as the reciprocal of the differentiation value is higher upon adding of the high-frequency components in the source image to the conversion image. In so doing, the processed image to be finally generated includes the high-frequency components, which realizes a conversion image having maintained contrast.

The second method is expressed as the following equation:

$$P1 = D_{conv}(P0) + (1/D_{conv}'(P0)) \times \Sigma LUT \quad (2)$$

Here, P0 indicates a source image, P1 a processed image, $\Sigma LUT$ high-frequency components in the source image, and $D_{conv}$ a function specified by the translation table.

However, a problem arises that the conventional first method cannot realize proper characteristic of dynamic range compression processing. Where the characteristic of dynamic range compression (compression characteristics) is modified, $D_{inv}$ in Equation (1) is to be modified. As is apparent from Equation (1), the function $D_{inv}$ operates on the image having the high-frequency components already contained therein. Consequently, where the intensity of dynamic range compression falls short in the high-frequency components, it is difficult to modify the function $D_{inv}$ for adjusting the compression characteristics only in the high-frequency components. As noted above, the function $D_{inv}$ operates on the image having the low and high-frequency components in the source image mixed therein. Accordingly, the compression characteristics is not modified independently among the low and high-frequency components. Thus, only the dynamic range compression processed image is acquired having decreased visibility.

Moreover, the conventional second method includes an index $D_{conv}'$ (P0) as weighting used in addition of the high-frequency components. The source image P0 contains noise components regardless of the subject image. According to the conventional second method, the noise components are considered in weighting used in addition of the high-frequency components. Accordingly, the processed image to be finally generated is disturbed by the noise components in the source image P0.

SUMMARY OF THE INVENTION

This invention has been made regarding the state of the art noted above, and its object is to provide an image processing method that allows image processing with better visibility and radiographic apparatus using the method.

This invention is constituted as stated below to achieve the above object. An image processing method according to this invention includes a band image generation step for generating band images through extracting a portion of frequency components in a source image having a subject image falling thereon; a lowest-frequency image generation step for generating a lowest-frequency image having a lowest-frequency component extracted from the source image; a lowest-frequency image control step for performing conversion processing to the lowest-frequency image in accordance with a lowest-frequency function to generate a lowest-frequency controlled image; a controlled band image generation step for performing conversion processing to the band image in accordance with a high-frequency function, that is different from the lowest-frequency function, to generate a controlled band image; and an image processing step for performing dynamic range compression processing to the source image using the lowest-frequency controlled image and the controlled band image.

Moreover, radiographic apparatus according to this invention includes a radiation source for emitting radiation; a radiation detecting device for detecting radiation; an image generation device for generating a source image having a subject image falling thereon in accordance with a detection signal outputted from the radiation detecting device; a band image generation device for generating band images through extracting a portion of frequency components in the source image; a lowest-frequency image generation device for generating a lowest-frequency image having a lowest-frequency component extracted from the source image; a lowest-frequency image control device for performing conversion processing to the lowest-frequency image in accordance with a lowest-frequency function to generate a lowest-frequency controlled image; a controlled band image generation device for performing conversion processing to the band image in accordance with a high-frequency function, that is different from the lowest-frequency function, to generate a controlled band image; and an image processing device for performing dynamic range compression processing to the source image using the lowest-frequency controlled image and the controlled band image.

According to the above configuration, two types of images are generated from the source image. One is the lowest-frequency image having the extracted lowest-frequency in the source image. The other is the band image having frequency components of the frequency components in the source image higher than those in the low frequency image. According to this invention, the lowest-frequency image is converted into the lowest-frequency controlled image in accordance with the lowest-frequency function. Subsequently the band image is converted into the controlled band image in accordance with the high-frequency function. Here, the lowest-frequency function is different from the high-frequency function. Consequently, the lowest-frequency image with the lowest-frequency component in the source image is controlled independently from the band images with the high-frequency components in the source image. As noted above, the lowest-frequency image and the band images independently controlled from each other are used in the dynamic range compression processing, which realizes proper performance of the dynamic range compression processing.

Moreover, in the foregoing image processing method, the high-frequency function in the controlled band image generation step is desirably determined in accordance with an index expressing inclination of the lowest-frequency function.

Furthermore, in the foregoing radiographic apparatus, the high-frequency function that the controlled band image generation device adopts is desirably determined in accordance with an index expressing inclination of the lowest-frequency function.

The foregoing configuration is a concrete example of the function for controlling the high-frequency. Where the dynamic range compression processing is performed through addition of the lowest-frequency controlled image and the source image, the low frequency components are partially lost from the source image. This loss occurs in a portion in the source image having a certain pixel value. The value corresponds to an input value having a high differentiation value of the lowest-frequency function. According to this invention, not only the lowest-frequency controlled image but also the band images having reversed high-frequency components are added to the source image, whereby relatively excessive high-frequency components derived from the source image may also be suppressed. In addition, the suppression is made while weighting is performed in accordance with the high differentiation value of the function for controlling the lowest-frequency. Consequently, the image to be finally acquired has better visibility due to suppression of only the relatively excessive high-frequency components therein.

Moreover, in the foregoing image processing method, it is more desirable that the lowest-frequency function in the lowest-frequency image control step is a function having a relationship between input values prior to the conversion processing and output values subsequent to the conversion processing. It is also more desirable that the output value increases or decreases monotonously relative to the input value.

Moreover, in the foregoing radiographic apparatus, it is more desirable that the lowest-frequency function that the lowest-frequency image control device adopts is a function having a relationship between input values prior to the conversion processing and output values subsequent to the conversion processing. It is also more desirable that the output value increases or decreases monotonously relative to the input value.

The foregoing configuration is a concrete example of the lowest-frequency function. Where the lowest-frequency function is a monotonically decreasing function, pixel data in the lowest-frequency image is to be reversed to generate a lowest-frequency controlled image. This is added to the source image, whereby a portion of the pixel data in both images is offset and the dynamic range compression processing is performed to the source image. The lowest-frequency function may be a monotonically increasing function depending on the forms of image processing.

Moreover, in the foregoing image processing method, the inclination of the lowest-frequency function in the lowest-frequency image control step is desirably "0" where the output value is "0".

Furthermore, in the foregoing radiographic apparatus, the inclination of the lowest-frequency function that the lowest-frequency image control device adopts is desirably "0" where the output value is "0".

The foregoing configuration is a concrete example of the lowest-frequency function. Where the output value is around a reference value of "0", the inclination of the lowest-frequency function is approximately "0". Accordingly, a portion of the pixel data close to the reference value is not subjected to the dynamic range compression processing. In so doing, only the pixel data in the source image that is extremely higher or lower than the reference value is converted to be lower or higher, respectively. Moreover, dynamic range compression processing may be performed while contrast around the reference value is maintained.

Moreover, the foregoing image processing method desirably includes the following. That is, the image processing method further includes a suppression image generation step for converting each of the band images into an absolute value suppression image having a suppressed absolute value of pixel data with use of a function for generating the absolute value suppression image. In the controlled band image generation step, the absolute value suppression image is used as the band image. In the suppression image generation step, the function for generating the suppression image has the output value varying monotonously relative to the input value.

Furthermore, the foregoing radiographic apparatus desirably includes the following configuration. That is, the radiographic apparatus further includes a suppression image generation device for converting each of the band images into an absolute value suppression image having a suppressed absolute value of pixel data with use of a function for generating the absolute value suppression image. The controlled band image generation device uses the absolute value suppression image as the band image. The function for generating the suppression image that the suppression image generation device adopts has the output value varying monotonously relative to the input value.

The foregoing configuration describes image processing in more detail. That is, the band image is once processed into the absolute value suppression image, and then is used for image processing. According to the foregoing configuration, image processing may be performed while the high-frequency components leading to no artifact are maintained.

Moreover, in the foregoing image processing method, the following is desirable. That is, when the function for generating the suppression image in the suppression image generation step is graphed, the output value monotonously increases relative to the input value symmetrically about an origin point, and inclination increases to approach "1" as the absolute value of the input value increases.

Furthermore, in the foregoing radiographic apparatus, the following configuration is desirable. That is, when the function for generating the suppression image that the suppression image generation device adopts is graphed, the output value monotonously increases relative to the input value symmetrically about an origin point, and inclination increases to approach "1" as the absolute value of the input value increases.

The foregoing configuration describes image processing in more detail. According to the function for generating the suppression image having the foregoing configuration, image processing may be performed more positively while the high-frequency components leading to no artifact are maintained.

Moreover, in the foregoing image processing method, it is more desirable that the controlled band image is generated in the controlled band image generation step in accordance with the lowest-frequency image.

Furthermore, in the foregoing radiographic apparatus, it is more desirable that the controlled band image generation device generates the controlled band image in accordance with the lowest-frequency image.

The foregoing configuration is a concrete example of generating the controlled band image. Upon determination of weighting in suppressing the relatively excessive high-frequency components derived from the source image, not the source image but the lowest-frequency image is used. If the source image is used, the source image containing noise components affects the dynamic range compression processing. Accordingly, weighting in the suppression is determined based on the lowest-frequency image containing no noise component as an index.

Moreover, in the foregoing image processing method, it is more desirable that at least one of the lowest-frequency function in the lowest frequency image control step, the high-frequency function in the controlled band image generation step, and the function for generating the suppression image in the suppression image generation step differs from each other depending on a site to be imaged in taking the source image or on types of operations.

Furthermore, in the foregoing radiographic apparatus, it is more desirable that at least one of the lowest-frequency function that the lowest-frequency image control device adopts, the high-frequency function that the controlled band image generation device adopts, and the function for generating the suppression image that the suppression image generation device adopts differs from each other depending on a site to be imaged in taking the source image or on types of operations.

Moreover, in the foregoing image processing method, it is more desirable that at least one of the lowest-frequency function in the lowest-frequency image control step, the high-frequency function in the controlled band image generation step, and the function for generating the suppression image in the suppression image generation step differs from each other depending on an amount of exposure in taking the source image.

Furthermore, in the foregoing radiographic apparatus, it is more desirable that at least one of the lowest-frequency function that the lowest-frequency image control device adopts, the high-frequency function that the controlled band image generation device adopts, and the function for generating the suppression image that the suppression image generation device adopts differs from each other depending on an amount of exposure in taking the source image.

Moreover, in the foregoing image processing method, it is more desirable that the dynamic range compression processing and image processing other than the dynamic range compression processing is performed in duplicate to the source image, and that at least one of the lowest-frequency function in the lowest-frequency image control step, the high-frequency function in the controlled band image generation step, and the function for generating the suppression image in the suppression image generation step differs from each other depending on types of image processing to the source image.

Furthermore, in the foregoing radiographic apparatus, it is more desirable that the image processing device performs the dynamic range compression processing and image processing other than the dynamic range compression processing in duplicate to the source image, and that at least one of the lowest-frequency function that the lowest frequency image control device adopts, the high-frequency function that the controlled band image generation device adopts, and the function for generating the suppression image that the suppression image generation device adopts differs from each other depending on types of image processing to the source image.

Moreover, in the foregoing image processing method, it is more desirable that at least one of the lowest-frequency function in the lowest-frequency image control step, the high-frequency function in the controlled band image generation step, and the function for generating the suppression image in the suppression image generation step differs from each other in each band image.

Furthermore, in the foregoing radiographic apparatus, it is more desirable that at least one of the lowest-frequency function that the lowest-frequency image control device adopts, the high-frequency function that the controlled band image generation device adopts, and the function for generating the suppression image that the suppression image generation device adopts differs from each other in each band image.

In each of the foregoing configurations, the lowest-frequency function that the lowest-frequency image control device adopts, the high-frequency function that the controlled band image generation device adopts, and the function for generating the suppression image that the suppression image generation device adopts vary depending on various conditions. In this way, image processing may be controlled with higher flexibility.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DESCRIPTION OF THE PREFERRED EMBODIMENTS

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

An embodiment of this invention will be described hereinafter. X-rays in the embodiment correspond to radiation in this invention. An FPD is the abbreviation of a flat panel detector.

<Whole Configuration of X-ray Apparatus>

Figure 1:
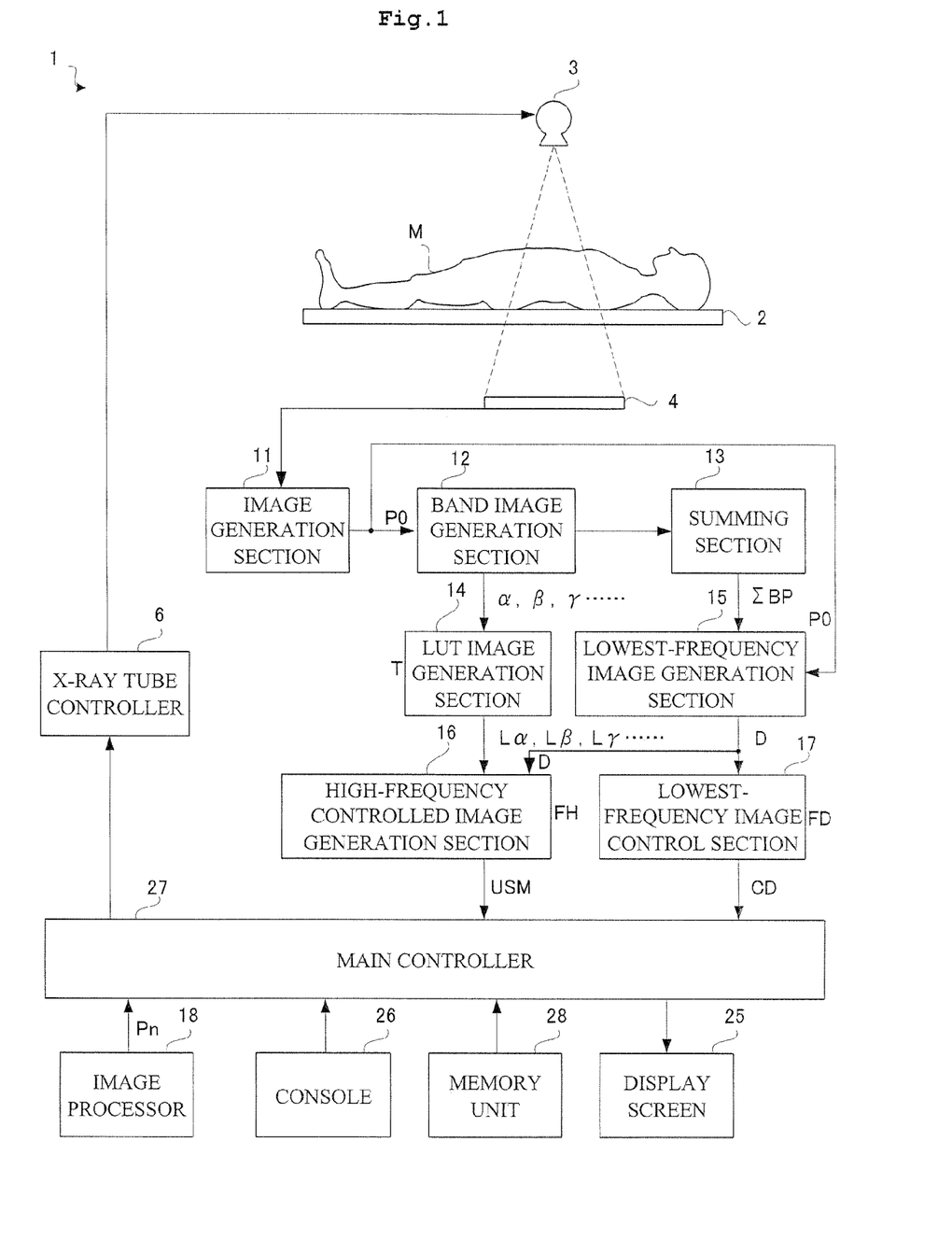
FIG. 1 is a functional block diagram illustrating a configuration of X-ray apparatus according to Embodiment 1.

Firstly, description will be given of a configuration of X-ray apparatus according to Embodiment 1. As shown in FIG. 1, the X-ray apparatus 1 includes a top board 2 for supporting a subject M placed thereon, an X-ray tube 3 above the top board 2 for emitting X-rays, and an FPD 4 below the top board 2 for detecting X-rays. The X-ray tube 3 corresponds to the radiation source in this invention. The FPD 4 corresponds to the radiation-detecting device in this invention.

An X-ray tube controller 6 is provided for controlling the X-ray tube 3 with a given tube current, a tube voltage, and a pulse width. The FPD 4 detects X-rays emitted from the X-ray tube 3 and transmitting through the subject M, and generates a detection signal. The detection signal is sent to an image generation section 11, where a source image P0 is generated having a projected image of the subject M falling thereon. A display unit 25 is provided for displaying the projected image of the subject M outputted from the image generation section 11. The image generation section 11 corresponds to the image generation device in this invention.

The X-ray apparatus 1 according to Embodiment 1 further includes a band image generation section 12, a summing section 13, a lowest-frequency image generation section 15, a lowest-frequency image control section 17, an LUT image generation section 14, a high-frequency controlled image generation section 16, and an image processor 18. The band image generation section 12 generates band images α, β, γ, . . . having frequency components in each band that are extracted from the source image P0. The summing section 13 sums up the band images α, β, γ, . . . to generate a sum image ΣBP. The lowest-frequency image generation section 15 generates a lowest-frequency image D from the source image P0 and the sum image ΣBP. The lowest-frequency image control section 17 converts the lowest-frequency image D into a lowest-frequency controlled image CD. The LUT image generation section 14 performs higher suppression to image data having a lower absolute value of the band images α, β, γ, . . . to generate a respective absolute value suppression image (LUT image Lα, Lβ, Lγ, . . . ). The high-frequency controlled image generation section 16 converts the LUT images Lα, Lβ, Lγ into a high-frequency controlled image USM, respectively. The image processor 18 performs image processing to the source image P0 using the lowest-frequency controlled image CD and the high-frequency controlled image USM to generate a processed image Pn.

The band image generation section 12 corresponds to the band image generation device in this invention, and the summing section 13 to the summing device in this invention. The LUT image generation section 14 corresponds to the suppression image generation device in this invention. The lowest-frequency image generation section 15 corresponds to the lowest-frequency image generation device in this invention. Moreover, the high-frequency controlled image generation section 16 corresponds to the controlled band image generation device in this invention. The lowest-frequency image control section 17 corresponds to the lowest-frequency image control device in this invention. The image processor 18 corresponds to the image processing device in this invention.

The LUT image L corresponds to the absolute value suppression image in this invention. The high-frequency controlled image USM corresponds to the controlled band image in this invention.

Figure 2:
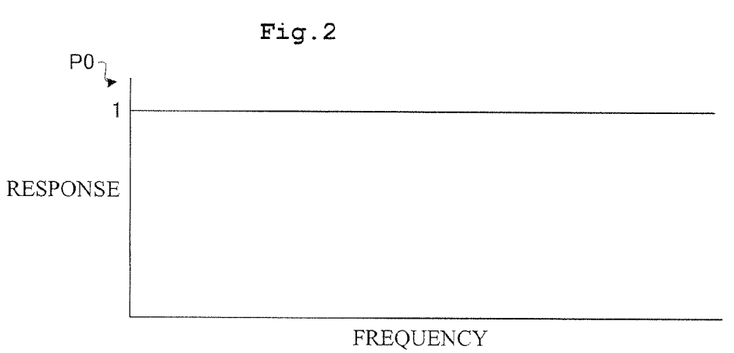
FIG. 2 is a schematic view illustrating frequency distribution of a source image according to Embodiment 1.
Figure 3:
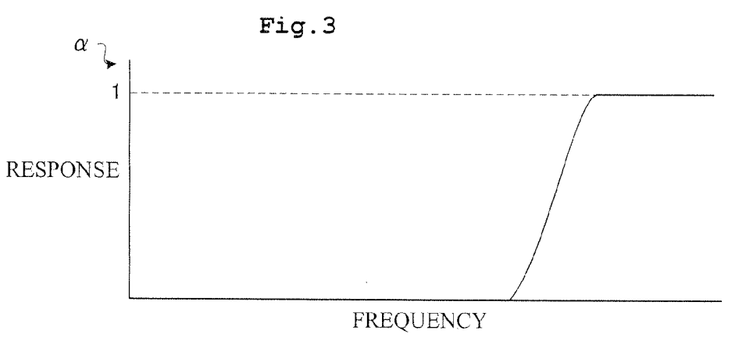
FIG. 3 to 5 are schematic views each illustrating frequency distribution of a band image according to Embodiment 1.
Figure 4:
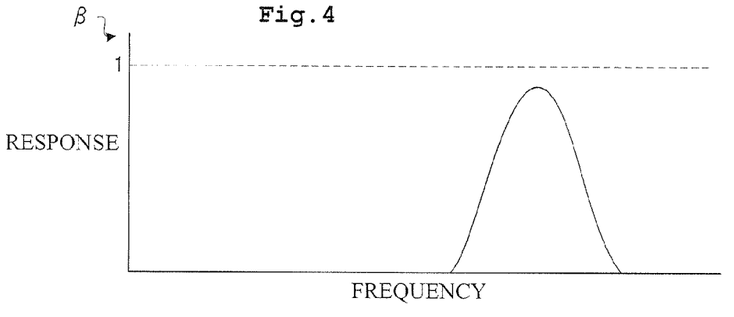
Figure 5:
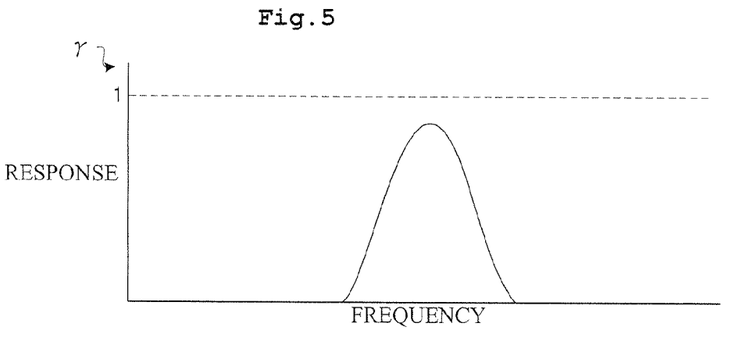

Next, description will be given of the band images α, β, and γ. FIG. 2 is the result of conducting frequency analysis of the source image P0. The source image P0 has wide frequency components from high frequencies to low frequencies. Here, for expediency of explanation, it is assumed that every frequency has a response of "1". FIG. 3 is the result of conducting frequency analysis of the first band image α. As illustrated in FIG. 3, the first band image α is an image having extracted frequency components in a highest frequency region in the source image β. FIG. 4 is the result of conducting frequency analysis of the second band image β. As illustrated in FIG. 4, the second band image β is an image having extracted frequency components in the secondary highest frequency region in the source image P0. FIG. 5 is the result of conducting frequency analysis of the third band image γ. As illustrated in FIG. 5, the third band image γ is an image having extracted frequency components in the thirdly highest frequency region in the source image P0. As above, the band images α, β, γ have the frequency components higher in this order that are derived from the source image P0.

Figure 6:
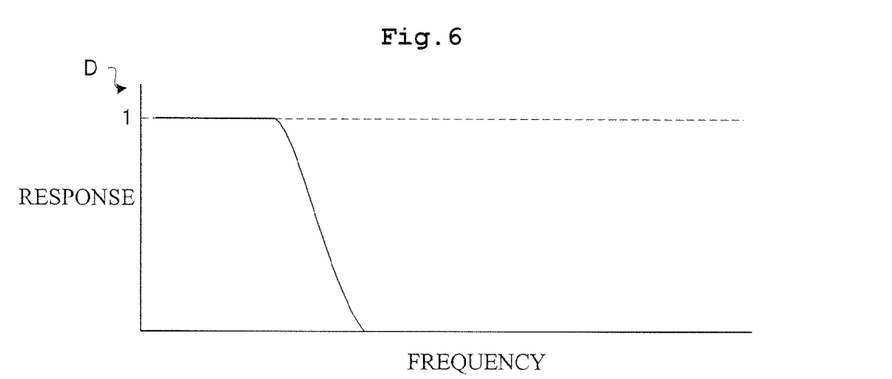
FIG. 6 is a schematic view illustrating frequency distribution of a lowest-frequency image according to Embodiment 1.

Description will be given of the lowest-frequency image D. FIG. 6 is the result of conducting frequency analysis of the lowest-frequency image D. As illustrated in FIG. 6, the lowest-frequency image D is an image having extracted frequency components in the highest frequency region in the source image P0.

A console 26 is provided for inputting operator's instructions such as start of emitting X-rays. Moreover, a main controller 27 is provided for performing an overall control of each controller. The main controller 27 has a CPU, and realizes the X-ray tube controller 6 and each section 11, 12, 13, 14, 15, 16, 17, 18 by executing various programs. The above sections may each be divided into arithmetic units that perform their functions. A memory unit 28 memorizes all parameters with respect to control and operation of the X-ray apparatus 1 such as a parameter used for image processing, an intermediate image generated in connection with the image processing, and a table.

Figure 7:
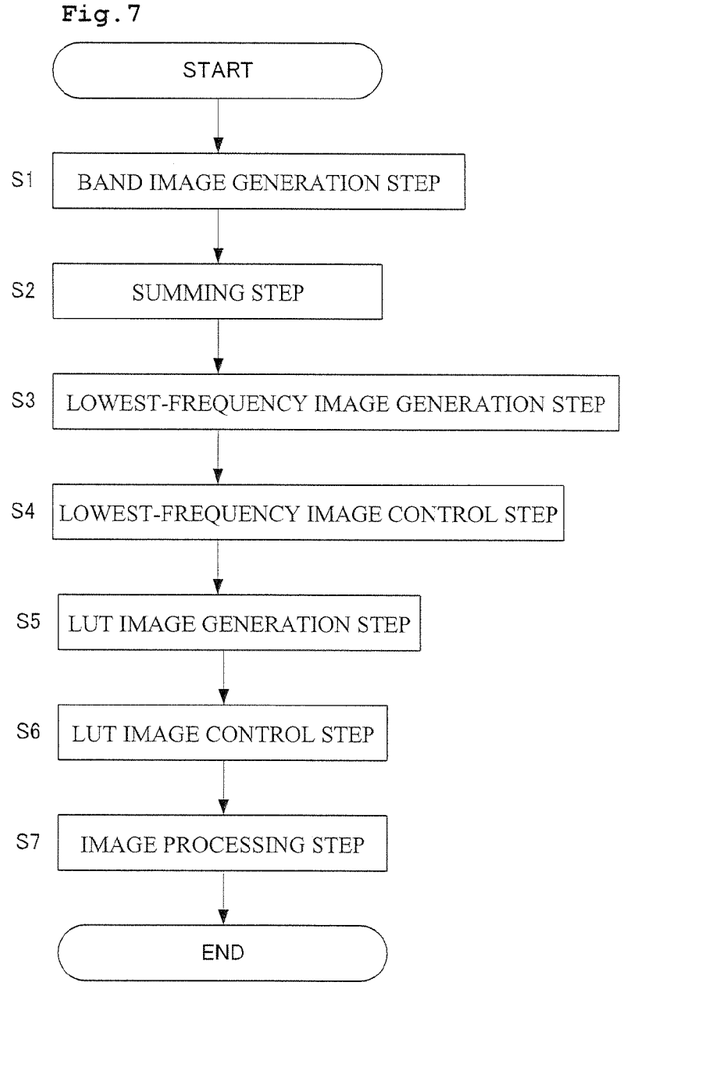
FIG. 7 is a flow chart illustrating operation of the X-ray apparatus according to Embodiment 1.

The band image generation section 12, the summing section 13, the LUT image generation section 14, the lowest-frequency image generation section 15, the high-frequency controlled image generation section 16, and the lowest-frequency image control section 17 perform a series of operations, thereby performing image processing such as dynamic range compression processing to the source image P0. Specifically, as illustrated in FIG. 7, the band images α, β, γ are firstly generated (a band image generation step S1), and then are summed (a summing step S2.) Thereafter, the lowest-frequency image D is generated based on the sum image ΣBP (a lowest-frequency image generation step S3), and is converted into the lowest-frequency controlled image CD (a lowest-frequency image control step S4.) Subsequently, the LUT image Lα, Lβ, Lγ is generated from the band image α, β, γ, respectively (an LUT image generation step S5), and is converted into the high-frequency controlled image USM (an LUT image control step S6.) Finally, image processing is performed based on the lowest-frequency controlled image CD and the high-frequency controlled image USM (an image processing step S7.) Description will be given of detailed operation in each step. The LUT image generation step S5 corresponds to the suppression image generation step in this invention. The LUT image control step S6 corresponds to the controlled band image generation step in this invention.

<Band Image Generation Step S1>

Figure 8:
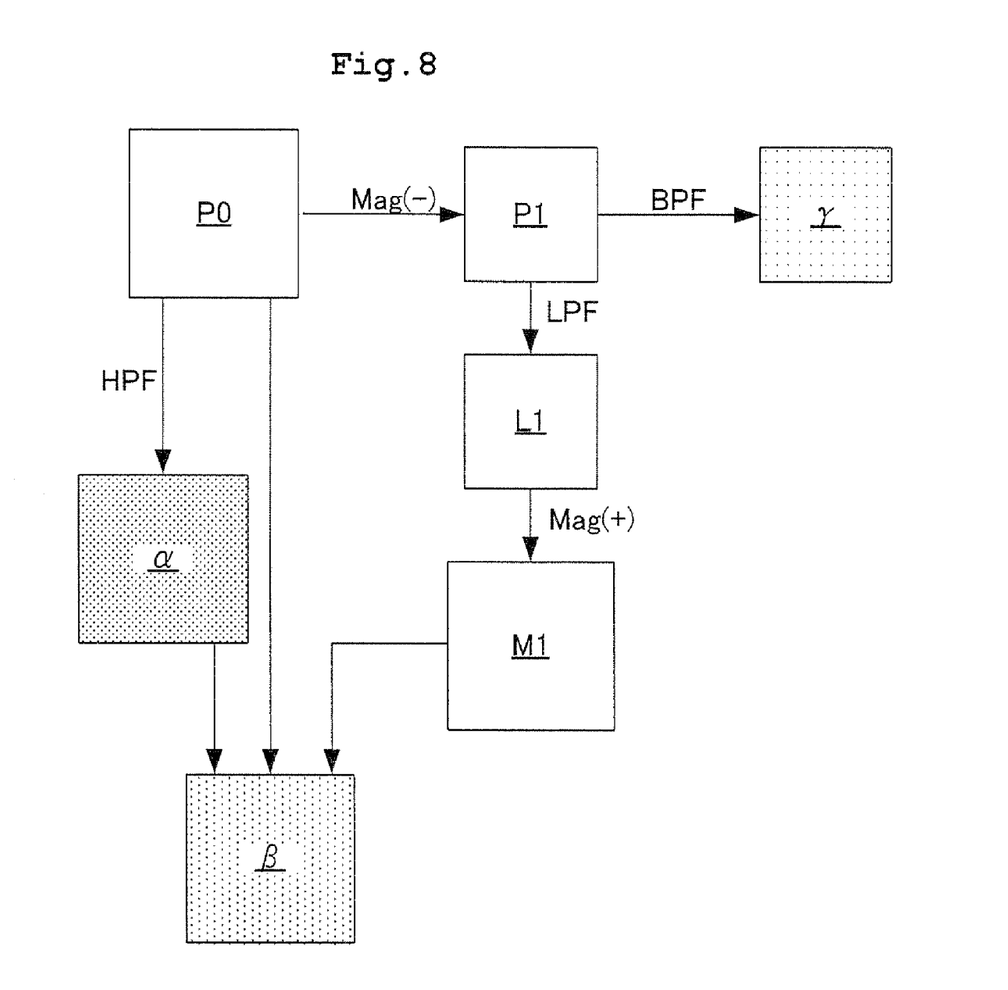
FIG. 8 to 17 are schematic views each illustrating operation of the X-ray apparatus according to Embodiment 1.

Description will be given of operations of the band image generation section 12. As illustrated in FIG. 8, the band image generation section 12 acquires a first band image α, a second band image β, and a third band image γ in this order. Each of these operations will be described in order. The method of generating the following band images α, β, γ is improvement of the conventional Laplacian pyramid decomposition.

Figure 9:
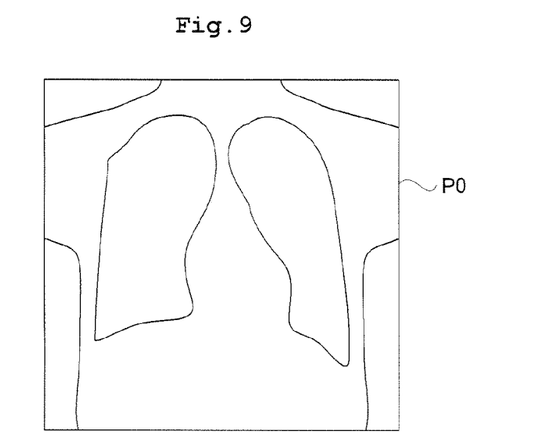
Figure 10:
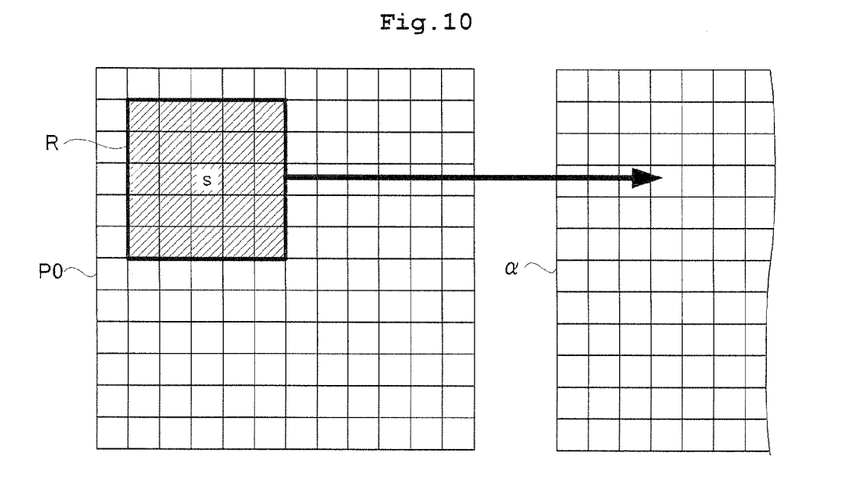

Firstly, description will be given of acquiring the first band image α. The source image P0 generated in the image generation section 11 (see FIG. 9) is sent to the band image generation section 12. The band image generation section 12 applies a matrix serving as a high-pass filter with respect to each of the pixels that form the source image P0. FIG. 10 illustrates a state where a pixel s forming the source image P0 is subjected to high-pass filter processing. The band image generation section 12 reads a matrix of 5 by 5, for example, for the high-pass filters from the memory unit 28, and applies the matrix to the pixel s. Accordingly, as illustrated in FIG. 10, the matrix is applied to a pixel region R of five rows and five columns having the pixel s as a center thereof. Thereafter, the band image generation section 12 puts pixel data obtained through application of the matrix to a position corresponding to the pixel s in the first band image α. The band image generation section 12 performs the same operation as above to all pixels, other than the pixel s, that form the source image P0. The acquired pixel data is brought into correspondence with the source image P0, and is mapped in the first band image α on each occasion. The high-pass filter transmits only the high-frequency components contained in the region R. Consequently, the first band image α becomes a rough image having the pixel data thereof varying finely. The high-pass filter processing is designated by the symbol HPF in FIG. 8.

Next, description will be given of acquiring the second band image β. As illustrated in FIG. 8, the band image generation section 12 generates a reduction image P1 by reducing the source image P0 by half vertically and horizontally. In FIG. 18, the process for educing an image is designated by the symbol Mag (−).

The band image generation section 12 performs low-pass filter processing to the reduction image P1. That is, the band image generation section 12 reads the matrix for the low-pass filter of 5 by 5 from the memory unit 28 having the same dimension as the matrix for the high-pass filters, and applies the matrix to each of the pixels forming the reduction image P1. The pixel data obtained through application of the matrix is brought into correspondence with the reduction image P1 and is mapped in the low-pass image L1, which situation is similar to the explanation using FIG. 10. Differences therebetween are the matrix to be used and the reduced size of the image. As noted above, frequency components may be extracted through reducing once the source image P0 and applying the low-pass filter even when the matrix specifying the band-pass filter does not increase in dimension. Consequently, a calculation cost may significantly be suppressed. The low-pass filter processing is designated by the symbol LPF in FIG. 8.

As illustrated in FIG. 8, the band image generation section 12 generates a magnified image M1 by magnifying the low-pass image L1 twice vertically and horizontally. In FIG. 8, the process for magnifying an image is designated by the symbol Mag (+). That is, the magnified low-pass image M1 has the same size as the source image P0. The band image generation section 12 generates the second band image β through subtraction of the first band image α and the magnified low-pass image M1 from the source image P0.

Figure 11:
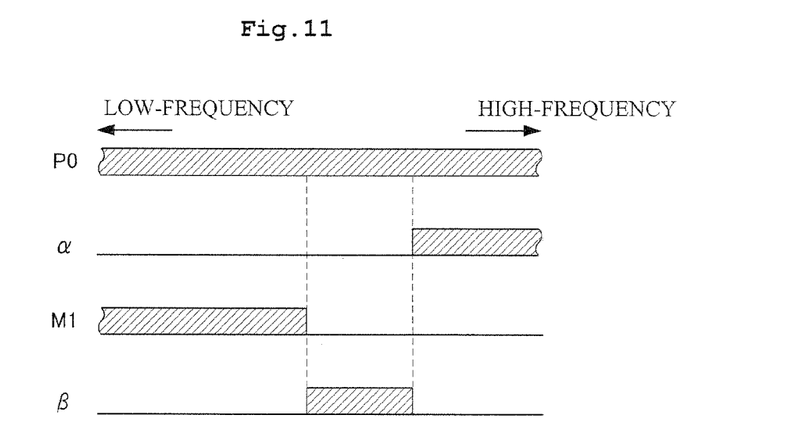

Description will be given of the second band image β. FIG. 11 is a schematic view illustrating a range of the frequency components contained in each image. As shown in FIG. 11, the source image P0 entirely has the frequency components. The first band image α contains only the high-frequency components, whereas the magnified low-pass image M1 is formed only of the low-frequency components in the reduction image P1. As illustrated in FIG. 11, the second band image β having the first band image α and the magnified low-pass image M1 subtracted from the source image P0 has frequency components among all frequency components of the source image P0 in a section between the lowest-frequency of the first band image α and the highest-frequency of the magnified low-pass image M1.

Description will be next given of the third band image γ. The band image generation section 12 reads the matrix for the band-pass filter of 9 by 9 from the memory unit 28 that is approximately twice the matrix for the low-pass filter, and applies the matrix to each of the pixels forming the reduction image P1. The pixel data obtained through application of the matrix is brought into correspondence with the reduction image P1, and is mapped in the third band image γ, which situation is similar to the explanation using FIG. 10. Differences therebetween are various types of matrix to be used, the matrix having appropriately twice the length and width, and the reduction image P1 to be processed having ¼ times the area of the source image P0. In FIG. 8, the band-pass filter processing is designated by the symbol BPF. The third band image γ generated as above additionally has extracted frequency components of the source image P0 in the lower frequency band than the second band image β.

The band image generation section 12 also generates a reduction image P2, other than the reduction image P1, that is obtained through reduction of the reduction image P1 by half vertically and horizontally. The reduction image P2 is also subjected to the band-pass filter processing, whereby a fourth band image δ is generated. The fourth band image δ generated as above additionally has extracted frequency components of the source image P0 in the lower frequency band than the third band image γ. In this way, the band image generation section 12 may generate the band image of the lower frequencies than the third band image γ. These band images may also be used for subsequent image processing. However, image processing is to be performed with the band images α, β, γ for simple explanation of Embodiment 1.

<Summing Step S2, Lowest-Frequency Image Generation Step S3>

The band images α, β, γ are sent to the summing section 13. The summing section 13 sums up the band images α, β, γ to generate the sum image ΣBP (see FIG. 1.) The sum image ΣBP is sent to the lowest-frequency image generation section 15. The lowest-frequency image generation section 15 also has the source image P0 already sent thereto from the image generation section 11. The lowest-frequency image generation section 15 generates the lowest-frequency image D through subtraction of the sum image ΣBP from the source image P0.

Figure 12:
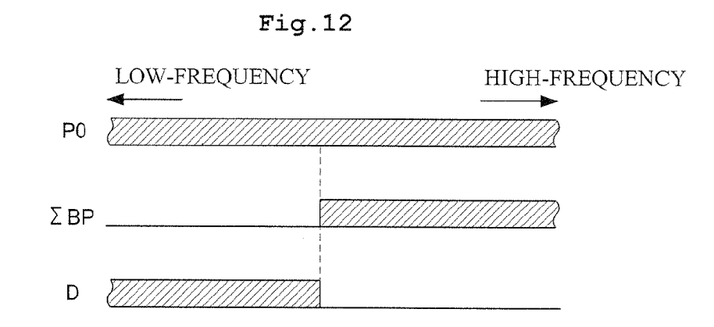

Description will be next given of the lowest-frequency image D. FIG. 12 is a schematic view illustrating a range of the frequency components contained in each image. As shown in FIG. 12, the source image P0 entirely has the frequency components. The sum image ΣBP contains no lowest-frequency component in the source image P0. The third band image γ as derivation of the lowest-frequency component in the sum image ΣBP is the output of the band-pass filter, and has no low frequency component in the source image. Consequently, the lowest-frequency component in the source image P0 is extracted upon subtraction of the sum image LW from the source image. Specifically, as illustrated in FIG. 12, the sum image ΣBP has further lower frequency components of all frequency components in the source image P0 than the lowest-frequency component in the third band image γ.

<Lowest-Frequency Image Control Step S4>

The lowest-frequency image D is sent to the lowest-frequency image control section 17. The lowest-frequency image control section 17 converts image data in the lowest-frequency image D, thereby generating the lowest-frequency controlled image CD. Here, the lowest-frequency image control section 17 reads out a lowest-frequency function FD memorized in the memory unit 28, and converts the lowest-frequency image D into the lowest-frequency controlled image CD in accordance with the function. The lowest-frequency function FD is memorized as a table in relation to input values and output values. Moreover, the function may be memorized as an equation, instead of the table. The lowest-frequency image control section 17 may read out the equation from the memory unit 28 to determine a relationship between the input values and the output values.

Figure 13:
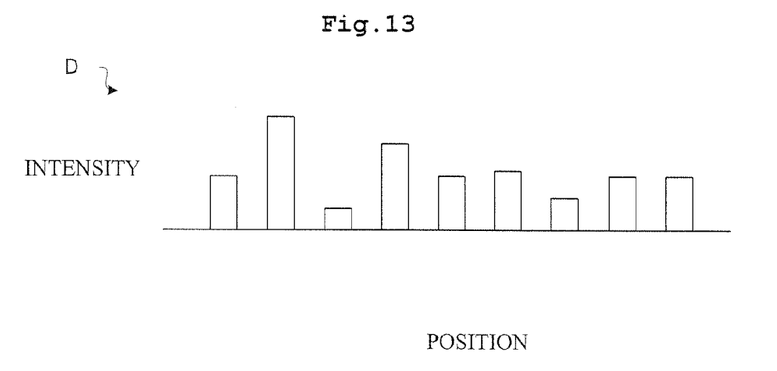

The lowest-frequency image D is formed of an array where a plurality of image data is arranged. Specifically, as illustrated in FIG. 13, the pixel data always has a positive value in accordance with a position of the image. Accordingly, the lowest-frequency function FD specifies the output value corresponding to the positive input value.

Figure 14:
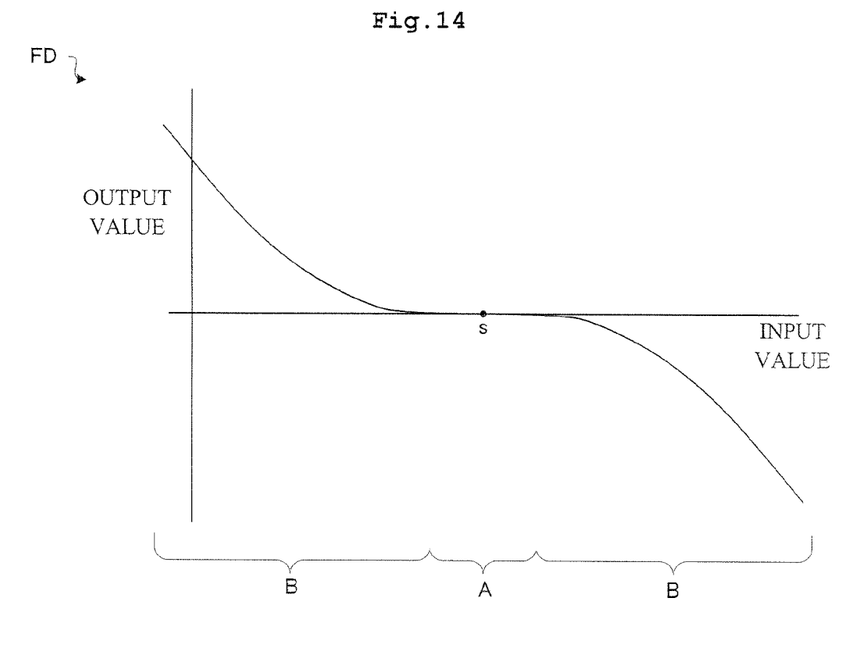

FIG. 14 is a graph illustrating a relationship between the input and output values of the lowest-frequency function FD. Inclination of the graph is "0" at the reference value s where the output values of the lowest-frequency function FD are "0". In addition, the lowest-frequency function FD is a monotonically decreasing function. The lowest-frequency function FD decreases rapidly as the input value increases from the reference value s. Conversely, the lowest-frequency function FD increases rapidly as the input value decreases from the reference value s. Accordingly, it is illustrated that applying of the lowest-frequency function FD to an image leads to output of an image having pixel data reversed about the reference value.

Figure 15:
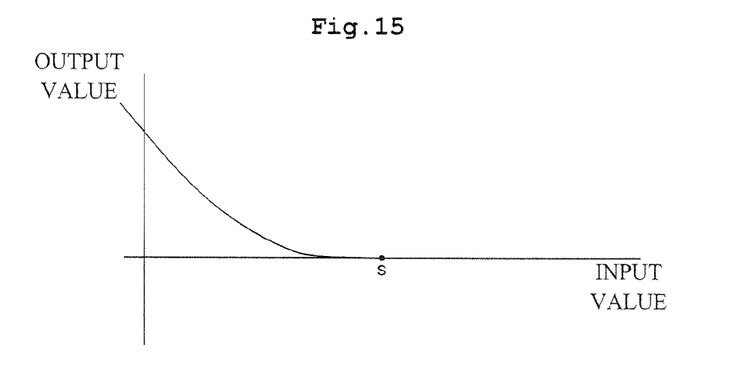

As another example of the lowest-frequency function FD, a function in the lowest-frequency function FD in FIG. 14 may be adopted having every output value of "0" relative to the input values with the reference value s or more (see FIG. 15.) In addition, a function may be adopted having every output value of "0" relative to the input values with the reference value s or less (see FIG. 16.)

Where an input value lies in a section A including the reference value s in FIG. 14, an output value is approximately "0". Where an input value lies in a section B apart from the reference value s, an output value (correctly, an absolute value thereof) is high. That is, a portion of the lowest-frequency image D the pixel data value close to the reference value s corresponds to a portion of the lowest-frequency controlled frequency image CD having the pixel data value of approximately "0". On the other hand, a portion in which the pixel data value in the lowest-frequency image D is apart from the reference value s corresponds to a portion having a high absolute value of the pixel data that is not equal to "0".

Where the dynamic range compression processing is performed through addition of the lowest-frequency controlled image CD to the source image P0, the pixel data is offset. That is because the lowest-frequency controlled image CD is a reverse image of the lowest-frequency image D generated based on the source image P0. The amount of offset, however, differs in portion of the source image P0. Specifically, offset is remarkably made to only portions in the lowest-frequency image D having the pixel data value apart from the reference value s (an extremely bright portion and an extremely dark portion.) That is, a higher value is added to the darker portion in the source image P0, and a higher value is added to the brighter portion. On the other hand, nothing is added to a gray portion in the source image P0 (close to the reference value s.) Consequently, the pixel data values in the source image having wide distribution are gathered around to the reference value s. In the actual operation, however, the dynamic range compression processing is not completed through merely adding the lowest-frequency controlled image CD and source image P0 to each other. That is because the image generated in such way has a partially excessive portion of the high-frequency components derived from the source image P0. Accordingly, the high-frequency controlled image USM, mentioned later, is added to the source image P0, whereby a partially excessive portion of the high-frequency components derived from the source image P0 may be removed.

<LUT Image Generation Step S5>

The band images α, β, γ generated by the band image generation section 12 are also sent to the LUT generation section 14. The LUT image generation 14 reads out an LUT image generation function T having related input and output values from the memory unit 28 for generating LUT images Lα, Lβ, Lγ from the band images α, β, γ, respectively, in accordance with the function T. This processing may suppress irregularities of the image appearing in the processed image Pn to be finally acquired. For instance, suppose that the band images α, β, γ are used as they are without generation of the LUT images Lα, Lβ, Lγ. Then, when the image generated from the band images α, β, γ and the source image P0 are superimposed for generation of the processed image Pn, a low positive or negative value of the band images α, β, γ is directly superimposed on the source image P0, which leads to decreased visibility of the processed image Pn. Such phenomenon may occur as follows. That is, where the image of the subject M having soft tissue to be highly subjected to the dynamic range compression processing falls on the source image P0, a contrast may readily decrease in the tissue of the subject M to which the dynamic range compression processing is performed. The soft tissue of the subject M in the source image P0 has no excessive high-frequency component contained therein. In the band images α, β, γ, the minute difference should be indicated as the frequency component. Specifically, a small absolute value of the pixel data is assigned to express the fine configuration. This is reversed and added in generation of the processed image Pn, which appears as a blurred false image. Accordingly, the LUT image generation section 14 performs higher suppression to a smaller absolute value of the pixel data that appears in the band images α, β, γ, whereby the LUT images Lα, Lβ, Lγ are generated.

Figure 16:
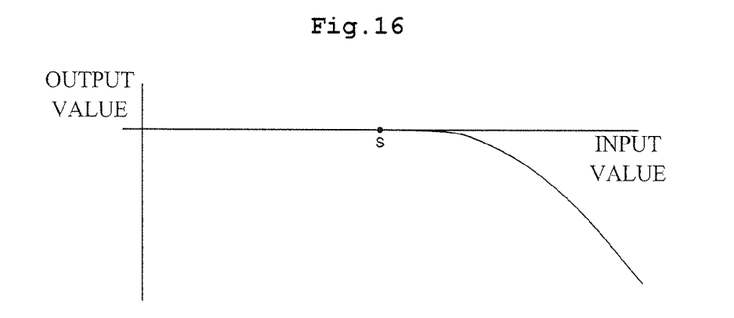
Figure 17:
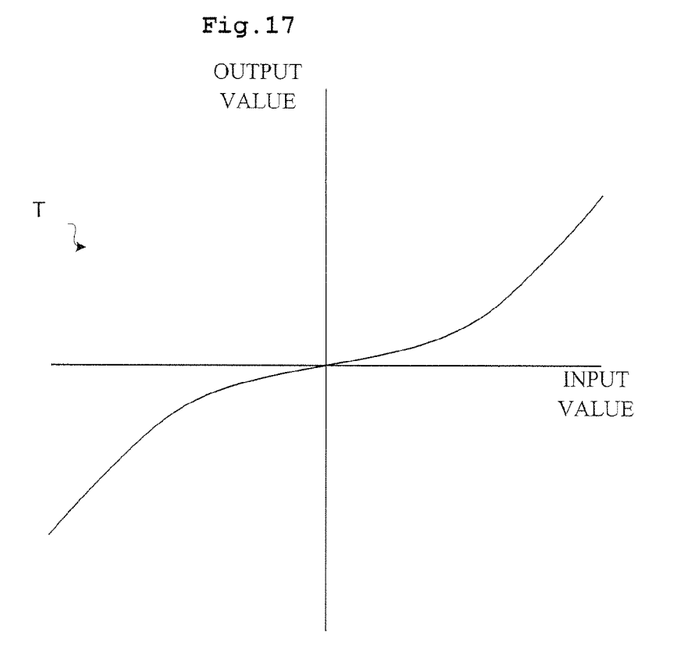

Description will be given of the LUT image generation function T that the LUT image generation section 14 adopts for the above conversion processing. FIG. 17 is a graph in relation to input values and output values of the LUT image generation function T. The graph is a nonlinear profile symmetric about an origin point. The LUT image generation section 14 reads the pixel data forming the band images α, β, γ, and sets it as an input value. Then, the LUT image generation section 14 acquires an output value from the LUT image generation function T at this time. The LUT image generation section 14 performs acquisition of the output value to every pixel data forming the first band image α, and maps the output values two-dimensionally, thereby acquiring a first LUT image Lα. Accordingly, the small absolute value in the first band image α may be removed. As shown in FIG. 15 or 16 above, the LUT images Lα, Lβ, Lγ have no pixel value of "0" when the band images α, β, γ have a large absolute value. In addition, the absolute value is suppressed in comparison with that of the band images α, β, γ.

The LUT image generation section 14 performs similar processing to the second band image β to generate a second LUT image Lβ. Likewise, the image processor 18 performs similar processing to the third band image γ to generate a third LUT image Lγ. In order to convert the band image α, β, γ two or more LUT image generation functions T may be selectively adopted. The same LUT image generation function T may be adopted in every band image α, β, γ.

Now, description will be given of characteristics of the LUT image generation function T. The LUT image generation function T has an output value monotonously increasing relative to an input value, and has minimum inclination where an input value is "0". The inclination increases gradually as the absolute value of the input value increases, and approaches "1".

<LUT Image Control Step S6>

The high-frequency controlled image generation section 16 also has the LUT image L and the lowest-frequency image D already sent thereto. Subsequently, the high-frequency controlled image generation section 16 adds them up for generating a suppression combined image ΣL. Here, the third LUT image Lγ differs from the other LUT images in size of the image, and thus they cannot be added up as they are. In this case, the high-frequency controlled image generation section 16 obtains an LUT sum image ΣL while appropriately magnifying the LUT images L. The sum LUT image ΣL contains high-frequency components derived from the source image P0 that the lowest-frequency image D does not have.

The lowest-frequency image D sent to the high-frequency controlled image generation section 16 is adopted for generating a coefficient map K. That is, the high-frequency controlled image generation section 16 generates a coefficient map K through application of the high-frequency function FH to the lowest-frequency image D. Thereafter, the high-frequency controlled image generation section 16 performs multiplication of the coefficient map K and the sum LUT image ΣL to generate a high-frequency controlled image USM. Here, the high-frequency controlled image generation section 16 reads out and adopts the high-frequency function FH memorized in the memory unit 28. The high-frequency function FH is memorized as a table having a relationship between the input values and the output values. Moreover, the function may be memorized as an equation, instead of the table. The high-frequency image generation section 16 may read out the equation from the memory unit 28 to determine a relationship between the input values and the output values. The high-frequency function FH corresponds to the high-frequency controlled image function in this invention.

Description will be given of a relationship between the lowest-frequency function FD and the high-frequency function FH. The high-frequency function FH is differential of the lowest-frequency function FD. The reason for the above will be described. As noted above, dynamic range compression processing is performed through addition of the lowest-frequency controlled image CD and the source image P0. Here, the lowest-frequency controlled image CD has no high-frequency component in the source image P0, but has reversed low-frequency components in the source image P0. Where the lowest-frequency component image CD and the source image P0 are added under this state, the processed image Pn to be generated has partially and relatively excessive frequency components, which causes overshoot in the processed image Pn.

In the processed image Pn, the high-frequency components are not readily excessive in a portion having the pixel data value of the lowest-frequency controlled image CD being approximately of "0". That is because the portion has nothing added to the pixel data in the source image P0 to be the processed image Pn. Rather, the processed image Pn has a tendency to have a portion of relatively excessive high frequency components due to removal of the low-frequency components where the relationship between the input values and the output values specified by a region B expressing an extremely high or low input value in FIG. 14 is adopted to generate the lowest-frequency controlled image CD. This portion indicates a strong tendency to convert the pixel values of the lowest-frequency function FD. As a result, addition of this portion to the source image P0 causes relative remaining of the high-frequency components in the source image P0 (an image edge.)

Accordingly, the high-frequency controlled image USM is generated for only suppression of the relatively excessive high-frequency components. The sum LUT image ΣL on which the generation is based includes reversed high frequency components that are relatively excessive due to addition of the lowest-frequency controlled image CD to the source image P0. However, mere addition of the sum LUT image ΣL as it is to the above two images may cause partially excessive addition of the high-frequency components. That is because the source image P0 partially differs in relatively excessive high-frequency component for addition of the lowest-frequency controlled image CD to the source image P0.

On the other hand, the high-frequency function FH is a function of differentiating the lowest-frequency function FD with respect to the input value. The high-frequency function FH is an index indicating how the high-frequency components are excessive by adding the lowest-frequency controlled image CD to the source image P0. Specifically, the high-frequency components are easy to be relatively excessive as the output value in the high-frequency function FH is higher at an input value.

Description will be given of the coefficient map K. The coefficient map K is generated through application of the high-frequency function FH to the lowest-frequency image D, and is a tendency map of the high-frequency components to be relatively excessive in superimposing of the source image P0 and the lowest-frequency controlled image CD.

The high-frequency controlled image generation section 16 performs multiplication of the coefficient map K and the sum LUT image ΣL to generate a high-frequency controlled image USM. Accordingly, the high-frequency controlled image USM is generated through weighting to the high-frequency components in the source image P0 in accordance with the tendency of the high-frequency components to be relatively excessive. Here, it is considered that the high-frequency controlled image USM is generated based on the LUT images L having an extracted pixel value where the band images α, β, γ have an extremely large absolute value. The high-frequency controlled image USM has a portion with no pixel value of "0" (or close thereto.) The portion in the high-frequency controlled image USM has a pixel value corresponding to the pixel value in the band image α, β, γ having an extremely large absolute value, the pixel value indicating a strong tendency to convert the pixel values of the lowest-frequency function FD. The portion in the high-frequency controlled image USM having no pixel value of "0" corresponds to the portion in the processed image Pn having excessive high-frequency components.

Moreover, it is notable that the coefficient map K is generated based on the lowest-frequency image D. That is, it is dared to use the lowest-frequency image D, although the same map is to be generated upon application of the high-frequency function FH to the source image P0. The reason is because the noise components are contained in the source image P0. The noise component is such as statistical noise and often appears in the source image P0 as a fine image. Even if the coefficient map K is generated with use of the source image P0, the coefficient takes an impossible value due to the noise component. Image processing with such coefficient may cause an image having decreased visibility. Accordingly, the coefficient map K is generated based on the lowest-frequency image D. The noise components in the source image P0 are mainly high-frequency components. Thus, the lowest-frequency image D hardly contains the noise components. Consequently, according to the configuration of Embodiment 1, a faithful coefficient map K may be generated under no influence of the noise.

<Image Processing Step S7>

The source image P0, the high-frequency controlled image USM, and the lowest-frequency controlled image CD are each sent to the image processor 18. The image processor 18 adds the source image P0, the high-frequency controlled image USM, and the lowest-frequency controlled image CD one another to generate the processed image Pn subjected to dynamic range compression processing.

Hereunder is an equation expressing operation of dynamic range compression processing in Embodiment 1.

$$Pn = P0 + FD(D) + FH(D) \cdot \Sigma L \qquad (3)$$

Here in the equation, Pn indicates a processed image Pn, and P0 a source image P0. FD indicates a lowest-frequency function FD, and D a lowest-frequency image D. FD (D) in the equation indicates a lowest-frequency controlled image CD, and expresses output of the lowest-frequency image control section 17. FH indicates a high-frequency function FH, and FH (D) in the equation indicates a coefficient map K. ΣL indicates a sum LUT image ΣL, and is equal to Lα+Lβ+Lγ.

<Operation of X-ray Apparatus>

Next, description will be given of operations of the X-ray apparatus 1. Firstly, the subject M is placed on the top board 2, and an operator instructs start of emitting radiation via the console 26. Then, the X-ray tube 3 emits X-rays, and the FPD 4 detects X-rays transmitting through the subject M. Here, the source image P0 is generated. The high-frequency controlled image USM and the lowest-frequency controlled image CD are generated based on the source image P0.

The operator instructs execution of image processing as the dynamic range compression processing via the console 26. The image processor 18 performs dynamic range compression processing through addition of the source image P0, the high-frequency controlled image USM, and the lowest-frequency controlled image CD in accordance with the operator's instructions. A projected image of the subject M having image processing performed thereto is displayed on a display screen 25, and operations of the X-ray apparatus 1 are completed.

According to the above configuration, two types of images are generated from the source image P0. One is the lowest-frequency image D having the extracted lowest-frequency in the source image P0. The other is the band image α, β, γ, having frequency components of the frequency components in the source image P0 higher than those in the low frequency image D. According to the configuration of Embodiment 1, the lowest-frequency image D is converted into the lowest-frequency controlled image CD in accordance with the lowest-frequency function FD. Subsequently, the band images α, β, γ are converted into the high-frequency controlled images USM in accordance with the high-frequency function FH. Here, the lowest-frequency function FD is a different function from the high-frequency function FH. Consequently, the lowest-frequency image D with the lowest-frequency component in the source image P0 is controlled independently from the band images α, β, γ with the high-frequency components in the source image P0. As noted above, the lowest-frequency image D and the band images α, β, γ independently controlled from each other are used in the dynamic range compression processing, which realizes proper performance of the dynamic range compression processing.

The foregoing configuration is a concrete example of the lowest-frequency function FD. Where the lowest-frequency function FD is a monotonically decreasing function, pixel data in the lowest-frequency image D is to be reversed to generate an lowest-frequency controlled image CD. This is added to the source image P0, whereby a part of the pixel data in both images is offset and the dynamic range compression processing is performed to the source image P0. The lowest-frequency function FD may be a monotonically increasing function depending on the forms of image processing.

The foregoing configuration is a concrete example of the lowest-frequency function FD. Where the output value is around a reference value of "0", the inclination in the lowest-frequency function FD is approximately "0". Accordingly, a portion having the input values close to the reference value is not subjected to the dynamic range compression processing. In so doing, only the pixel data values in the source image P0 that is extremely apart from the reference value is suppressed to be around the reference value, whereby dynamic range compression processing may be performed.

The foregoing configuration is a concrete example of the high-frequency function FH. Where the dynamic range compression processing is performed through addition of the lowest-frequency controlled image CD and the source image P0, the low-frequency components are partially lost from the source image P0. This loss occurs in a portion in the source image P0 having a certain pixel value. The value corresponds to an input value having a differentiation value of the lowest-frequency function FD. According to the configuration of Embodiment 1, not only the lowest-frequency controlled image CD and the source image P0 but also the band images α, β, γ having high frequency components (more correctly, the LUT images L) are added to one another, whereby relatively excessive high-frequency components derived from the source image P0 may also be suppressed. In addition, the suppression is made while weighting is performed in accordance with the high differentiation value of the lowest-frequency function FD. Consequently, the image to be finally acquired has better visibility due to suppression of only the relatively excessive high frequency components therein.

The foregoing configuration is a concrete example of generating the high-frequency controlled image USM. Upon determination of weighting in suppressing the relatively excessive high-frequency components derived from the source image P0, not the source image P0 but the lowest-frequency image D is used. If the source image P0 is used, the source image P0 containing noise components affects the dynamic range compression processing. Accordingly, weighting in the suppression is determined based on the lowest-frequency image D containing no noise component as an index.

The foregoing configuration describes in more detail a configuration of image processing. That is, the band image α, β, γ is once processed into the LUT image L, and then is used for image processing. In so doing, contrast never decreases in a portion having not so excessive high-frequency components in the source image P0.

This invention is not limited to the foregoing configuration, but may be modified as follows:

(1) In the foregoing configuration, FD(D) and FH(D)·ΣL is added to P0 as they are in Equation (3). An operator may select how the dynamic range compression processing is performed. The operator sets gain G via the console 26. The image processor 18 performs weighting to FD (D) and FH(D)·ΣL in accordance with gain G, and adds it to P0. In so doing, merely varying of a single value allows simple control of dynamic range compression processing. The image processing that the image processor 18 performs in this case is expressed as the following equation:

$$Pn=P0+G(FD(D)+FH(D)\cdot\Sigma L) \quad (4)$$

Here, G indicates gain G.

(2) According to the foregoing configuration, the lowest-frequency function FD having a relationship between the input values and the output values is a monotonically decreasing function. This invention is not limited to this embodiment. The lowest-frequency function FD may be a monotonically increasing function depending on variation in addition of the images by the image processor 18.

(3) According to the foregoing configuration, the high-frequency function FH is a function of differentiating the lowest-frequency function FD. This invention is not limited to this embodiment. Instead of setting the high-frequency function FH as differentiation of the lowest-frequency function FD, the high-frequency function FH may be set using another index indicating inclination of the lowest-frequency function FD. For instance, the high-frequency function FH may be a moving average of the differentiation values of the lowest-frequency function FD.

(4) In addition to the foregoing configurations, at least one of the lowest-frequency function FD, the high-frequency function FH, and the LUT image generation function T may vary depending on a site to be imaged or on types of operations. Specifically, the source image P0 contains data on a site to be imaged or types of operations. The LUT image generation section 14, the lowest-frequency image generation section 15, and the high-frequency controlled image generation section 16 read out the data for determination of the function or table to be used. Each section 14, 15, and 16 uses a correlated table having a relationship between the function or table that the memory unit 28 memorizes and the site to be imaged or types of operations, whereby the determination is made.

(5) In addition to the foregoing configurations, at least one of the lowest-frequency function FD, the high-frequency function FH, and the LUT image generation function T may vary depending on an amount of exposure (an amount of X-rays) in taking the source image P0. Specifically, the source image P0 contains data on an amount of X-rays. Each section 14, 15, and 16 read out the data on an amount of X-rays for determination of the function or table to be used. Each section 14, 15, and 16 uses a correlated table having a relationship between the function or table that the memory unit 28 memorizes and the amount of X-rays, whereby the determination is made.

(6) In addition to the foregoing configuration, at least one of the lowest-frequency function FD, the high-frequency function FH, and the LUT image generation function T may vary in each of the band images α, β, γ. Each section 14, 15, and 16 uses a correlated table having a relationship between the function or table that the memory unit 28 memorizes and the band images α, β, γ, whereby the variation is made.

(7) In addition to the foregoing configurations, at least one of the lowest-frequency function FD, the high-frequency function FH, and the LUT image generation function T may vary depending on image processing to be performed to the source image P0. The image processing section 18 occasionally performs to the source image P0 not only dynamic range compression processing but also another image processing, such as high-frequency emphasis processing, prior or subsequent to the processing in duplicate. Accordingly, appearance of the high-frequency components may sometimes vary in the image to be finally acquired. The lowest-frequency function FD, the high-frequency function FH, and the LUT image generation function T may vary depending on types of image processing other than the dynamic range compression processing, whereby a processed image having good visibility may be provided under variation of the image processing. Each section 14, 15, and 16 uses a correlated table having a relationship between the function or table that the memory unit 28 memorizes and types of image processing, whereby the variation is made.

(8) In the foregoing configurations, the LUT image L is generated based on the band images α, β, γ. This process may be omitted, which operation is expressed as the following equation:

$$Pn=P0+FD(D)+FH(D)\cdot(\alpha+\beta+\gamma) \qquad (5)$$

Here, α, β, γ in Equation (5) indicates the band image α, β, γ.

(9) The correlated table in relation to the input and output values may be adopted instead of the LUT image generation function T, the lowest-frequency function FD, and the high-frequency function FH. The memory unit 28 memorizes the correlated table. The LUT image generation section 14, the high-frequency controlled image generation section 16, and the lowest-frequency image control section 17 read out the correlated table from the memory unit 28 to use them for operations.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An image processing method for performing dynamic range compression processing to a source image, comprising:
    a band image generation step for generating band images through extracting a portion of frequency components in the source image having a subject image falling thereon;
    a lowest-frequency image generation step for generating a lowest-frequency image having a lowest-frequency component extracted from the source image;
    a lowest-frequency image control step for performing conversion processing to the lowest-frequency image in accordance with a lowest-frequency function to generate a lowest-frequency controlled image;
    a controlled band image generation step for performing conversion processing to the band image in accordance with a high-frequency function, that is different from the lowest-frequency function, to generate a controlled band image; and
    an image processing step for performing dynamic range compression processing to the source image using the lowest-frequency controlled image and the controlled band image.

2. The image processing method according to claim 1, wherein
    the high-frequency function in the controlled band image generation step is determined in accordance with an index expressing inclination of the lowest-frequency function.

3. The image processing method according to claim 1, wherein
    the lowest-frequency function in the lowest-frequency image control step is a function having a relationship between input values prior to the conversion processing and output values subsequent to the conversion processing, and
    the output value increases or decreases monotonously relative to the input value.

4. The image processing method according to claim 3, wherein
    the inclination of the lowest-frequency function in the lowest-frequency image control step is "0" where the output value is "0".

5. The image processing method according to claim 1, further comprising a suppression image generation step for converting each of the band images into an absolute value suppression image having a suppressed absolute value of pixel data with use of a function for generating the absolute value suppression image, wherein
    in the controlled band image generation step, the absolute value suppression image is used as the band image, and
    in the suppression image generation step, the function for generating the suppression image has the output value varying monotonously relative to the input value.

6. The image processing method according to claim 5, wherein
    where the function for generating the suppression image in the suppression image generation step is graphed, the output value monotonously increases relative to the input value symmetrically about an origin point, and inclination increases to approach "1" as the absolute value of the input value increases.

7. The image processing method according to claim 1, wherein
    the controlled band image is generated in the controlled band image generation step in accordance with the lowest-frequency image.

8. The image processing method according to claim 5, wherein
    at least one of the lowest-frequency function in the lowest frequency image control step, the high-frequency function in the controlled band image generation step, and the function for generating the suppression image in the suppression image generation step differs from each other depending on a site to be imaged in taking the source image or on types of operations.

9. The image processing method according to claim 5, wherein
    at least one of the lowest-frequency function in the lowest-frequency image control step, the high-frequency function in the controlled band image generation step, and the function for generating the suppression image in the suppression image generation step differs from each other depending on an amount of exposure in taking the source image.

10. The image processing method according to claim 5, wherein
- the dynamic range compression processing and image processing other than the dynamic range compression processing is performed in duplicate to the source image, and
- at least one of the lowest-frequency function in the lowest-frequency image control step, the high-frequency function in the controlled band image generation step, and the function for generating the suppression image in the suppression image generation step differs from each other depending on types of image processing to the source image.

11. The image processing method according to claim 5, wherein
- at least one of the lowest-frequency function in the lowest-frequency image control step, the high-frequency function in the controlled band image generation step, and the function for generating the suppression image in the suppression image generation step differs from each other in each band image.

12. Radiographic apparatus for performing dynamic range compression processing to a source image, comprising:
- a radiation source for emitting radiation;
- a radiation detecting device for detecting radiation;
- an image generation device for generating the source image having a subject image falling thereon in accordance with a detection signal outputted from the radiation detecting device;
- a band image generation device for generating band images through extracting a portion of frequency components in the source image;
- a lowest-frequency image generation device for generating a lowest-frequency image having a lowest-frequency component extracted from the source image;
- a lowest-frequency image control device for performing conversion processing to the lowest-frequency image in accordance with a lowest-frequency function to generate a lowest-frequency controlled image;
- a controlled band image generation device for performing conversion processing to the band image in accordance with a high-frequency function, that is different from the lowest-frequency function, to generate a controlled band image; and
- an image processing device for performing dynamic range compression processing to the source image using the lowest-frequency controlled image and the controlled band image.

13. The radiographic apparatus according to claim 12, wherein
- the high-frequency function that the controlled band image generation device adopts is determined in accordance with an index expressing inclination of the lowest-frequency function.

14. The radiographic apparatus according to claim 12, wherein
- the lowest-frequency function that the lowest-frequency image control device adopts is a function having a relationship between input values prior to the conversion processing and output values subsequent to the conversion processing, and
- the output value increases or decreases monotonously relative to the input value.

15. The radiographic apparatus according to claim 14, wherein
- the inclination of the lowest-frequency function that the lowest-frequency image control device adopts is "0" where the output value is "0".

16. The radiographic apparatus according to claim 12, further comprising a suppression image generation device for converting each of the band images into an absolute value suppression image having a suppressed absolute value of pixel data with use of a function for generating the absolute value suppression image, wherein
- the controlled band image generation device uses the absolute value suppression image as the band image, and
- the function for generating the suppression image that the suppression image generation device adopts has the output value varying monotonously relative to the input value.

17. The radiographic apparatus according to claim 16, wherein
- where the function for generating the suppression image that the suppression image generation device adopts is graphed, the output value monotonously increases relative to the input value symmetrically about an origin point, and inclination increases to approach "1" as the absolute value of the input value increases.

18. The radiographic apparatus according to claim 12, wherein
- the controlled band image generation device generates the controlled band image in accordance with the lowest-frequency image.

19. The radiographic apparatus according to claim 16, wherein
- at least one of the lowest-frequency function that the lowest-frequency image control device adopts, the high-frequency function that the controlled band image generation device adopts, and the function for generating the suppression image that the suppression image generation device adopts differs from each other depending on a site to be imaged in taking the source image or on types of operations.

20. The radiographic apparatus according to claim 16, wherein
- at least one of the lowest-frequency function that the lowest-frequency image control device adopts, the high-frequency function that the controlled band image generation device adopts, and the function for generating the suppression image that the suppression image generation device adopts differs from each other depending on an amount of exposure in taking the source image.

21. The radiographic apparatus according to claim 16, wherein
- the image processing device performs the dynamic range compression processing and image processing other than the dynamic range compression processing in duplicate to the source image, and
- at least one of the lowest-frequency function that the lowest frequency image control device adopts, the high-frequency function that the controlled band image generation device adopts, and the function for generating the suppression image that the suppression image generation device adopts differs from each other depending on types of image processing to the source image.

22. The radiographic apparatus according to claim 16, wherein at least one of the lowest-frequency function that the lowest-frequency image control device adopts, the high-frequency function that the controlled band image generation device adopts, and the function for generating the suppression image that the suppression image generation device adopts differs from each other in each band image.

\* \* \* \* \*